United States Patent
Nishiyama et al.

(10) Patent No.: US 8,962,854 B2
(45) Date of Patent: Feb. 24, 2015

(54) LUMINESCENT SUBSTRATE FOR LUCIFERASE

(75) Inventors: Shigeru Nishiyama, Yokohama (JP); Tsuyoshi Saito, Yokohama (JP); Shojiro Maki, Setagaya-ku (JP); Haruki Niwa, Mitaka (JP)

(73) Assignee: The University of Electro-Communications, Tokyo (JP)

( * ) Notice: Subject to any disclaimer, the term of this patent is extended or adjusted under 35 U.S.C. 154(b) by 0 days.

(21) Appl. No.: 14/240,144

(22) PCT Filed: Aug. 22, 2012

(86) PCT No.: PCT/JP2012/071207
§ 371 (c)(1),
(2), (4) Date: Mar. 28, 2014

(87) PCT Pub. No.: WO2013/027770
PCT Pub. Date: Feb. 28, 2013

(65) Prior Publication Data
US 2014/0221665 A1  Aug. 7, 2014

(30) Foreign Application Priority Data
Aug. 24, 2011 (JP) ................................ 2011-182224

(51) Int. Cl.
*C07D 417/04* (2006.01)
*C07D 417/06* (2006.01)
*C07D 277/10* (2006.01)
*C07D 277/66* (2006.01)
*C12Q 1/66* (2006.01)
*C07D 277/12* (2006.01)
*A61K 49/00* (2006.01)

(52) U.S. Cl.
CPC ............... *C12Q 1/66* (2013.01); *C07D 417/04* (2013.01); *C07D 417/06* (2013.01); *C07D 277/12* (2013.01); *C07D 277/66* (2013.01); *A61K 49/003* (2013.01)
USPC ......................................... 548/178; 548/201

(58) Field of Classification Search
USPC ................................................ 548/178, 201
See application file for complete search history.

(56) References Cited

U.S. PATENT DOCUMENTS 7,524,876 B2    4/2009   Takakura et al.
2007/0015790 A1 1/2007   Cali et al.

FOREIGN PATENT DOCUMENTS

| JP | A-2006-219381 | 8/2006 |
| JP | A-2007-91695 | 4/2007 |
| JP | A-2008-545746 | 12/2008 |
| JP | A-2010-180191 | 8/2010 |
| JP | A-2010-215795 | 9/2010 |
| WO | WO 2007/116687 A1 | 10/2007 |
| WO | WO 2010/106896 A1 | 9/2010 |

OTHER PUBLICATIONS

Chemical Abstracts Registry No. 1388733-69-4, indexed in the Registry file on STN CAS ONLINE Aug. 9, 2012.*
Takakura et al. CA 157:285955, 2012.*
Promega KK General Catalogue, Sep. 2008, "Chromo-Luc™ Vector & Chromo-Glo™ Assay," (with partial translation).
"MultiReporter Assay System—Tripluc™," *Upoload Toyobo Biochemicals*, vol. 79, 2005, pp. 1-10 and 2006/2007, pp. 4-67 (with partial translation).
Promega KK General Catalogue, Sep. 2008, pp. 12.4, 12.6 &12.7 (with partial translation).
ATTO Corporation General Catalogue, 2008-2009, p. 247 (with partial translation).
Takakura et al., "Development of 5'- and 7'-Substituted Luciferen Analogues as Acid-Tolerant Substrates of Firefly Luciferase," *Chembiochem*, 2012, vol. 13, pp. 1424-1427, with Supporting Information,. S1-S16.
International Search Report issued in International Patent Application No. PCT/JP2012/071207 dated Sep. 18, 2012.
Oct. 24, 2014 Office Action issued in Chinese Patent Application No. 201280041269.3 (with English translation).

* cited by examiner

*Primary Examiner* — Laura L. Stockton
(74) *Attorney, Agent, or Firm* — Oliff PLC

(57) ABSTRACT

An object of the present invention to provide a firefly luciferin and firefly luciferin analog that are modified to maintain luminescent activity by luciferase in a firefly bioluminescent system. In particular, it is an object of the present invention to provide a new luminescent substrate for which the emission wavelength in a firefly bioluminescent system is shifted to a longer wavelength than that of a conventional luminescent substrate. The present invention provides a luciferin in which the benzothiazole ring moiety has been modified at the 7-position, a luciferin analog in which the benzene ring moiety has been modified at the 6-position, and a luciferin analog in which the 6-(dialkylamino)-2-naphthalenyl moiety has been modified at the 5-position.

10 Claims, 1 Drawing Sheet

FIG. 1

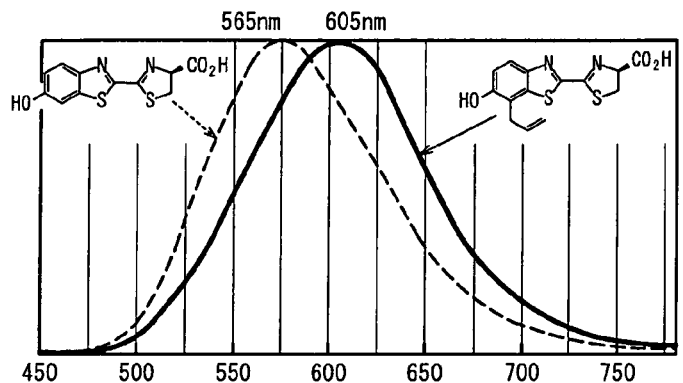

| | Concentration | Volume (μl) | Final concentration |
|---|---|---|---|
| Photnus pylalis (Promega KK) | 1mg/ml | 5 | 0.2mg/ml |
| Substrate | 100 μM | 5 | 20 μM |
| pH8 potassium phosphate buffer solution | 500mM | 5 | 100mM |
| Mg-ATP | 200 μM | 10 | 80 μM |

Measurement device AB-1850 (ATTO Corporation, CCD)

FIG. 2

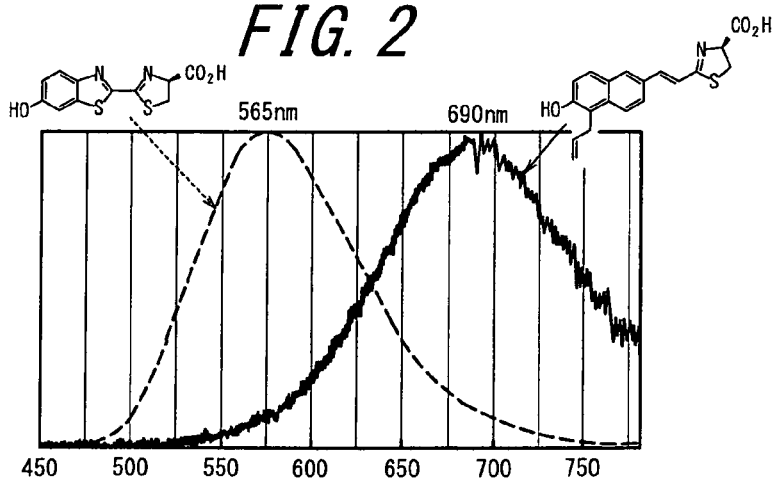

| | Concentration | Volume (μl) | Final concentration |
|---|---|---|---|
| Photnus pyiri (Promega KK) | 1mg/ml | 5 | 0.2mg/ml |
| Substrate | 100 μM | 5 | 20 μM |
| pH8 potassium phosphate buffer solution | 500mM | 5 | 100mM |
| Mg-ATP | 200 μM | 10 | 80 μM |

Measurement device AB-1850 (ATTO Corporation, CCD)

LUMINESCENT SUBSTRATE FOR LUCIFERASE

TECHNICAL FIELD

The present invention relates to a luciferin analog. More particularly, the present invention relates to a luciferin analog modified so that the emission wavelength due to luciferase is shifted to a longer wavelength.

BACKGROUND ART

<About Firefly Luciferin>

In recent years, the visualization of biological events and phenomena have been considered to be important, and a demand has increased for an expansion of materials for visualization. At the same time, there is the demand for diversification of labeling techniques. In particular, labeling techniques for molecular imaging have been greatly developed in conjunction with progress in equipment of diagnoses and examinations. For example, labeling techniques that can be applied to cutting-edge technology, such as individualized medical care for cancer or heart disease, are being intensely researched. Along with progress in measurement techniques, the demand for higher-sensitivity and higher-performance equipment and labeling materials is quickly rising.

Among visualization techniques, a firefly bioluminescent system is considered to have an extremely high luminous efficiency and to be the system that most efficiently converts energy into light. Progress is also being made into deciphering the molecular mechanism of bioluminescence.

With a firefly bioluminescence, it is known that light is emitted due to a chemical reaction of luciferin, which is a luminescent substrate, by the action of luciferase which is the luminescent enzyme. In this reaction, the luminescent substrate is adenylylated (converted to AMP) within the luminescent enzyme in the presence of adenosine triphosphate (ATP) and divalent magnesium ions ($Mg^{2+}$) and is derived into an adenylylated form, which is an active substrate. Next, this form is oxygenated, yielding a peroxide anion, and converted into dioxetanone, which is a high-energy peroxide. Unstable dioxetanone releases protons and carbon dioxide while decomposing and adopts an excited singlet state. The light emitted from this dianion-type excited singlet state is yellowish green, which is considered to be firefly light. The product after light emission is referred to as oxyluciferin.

As described above, the firefly bioluminescence has an extremely high luminous efficiency, and progress is being made into deciphering the molecular mechanism of bioluminescence. Therefore, a wide variety of luminescent material using a firefly bioluminescent system is being sold by many companies. In the development of luminescent material related to a firefly bioluminescence, however, the commercialization has mainly progressed in the field of medical biochemistry. Hence, while much research and development focuses in general on proteins (enzymes), very little research deals with low-molecular compounds (substrates). In particular, almost no correlation studies have been performed between an activity and a structure in which a luminescent substrate has undergone skeletal transformations.

Furthermore, even though luminescent enzymes can be supplied at low cost with a recombination technique, a luminescent labeling material using a firefly bioluminescent system supplied by a kit product or the like is expensive. The reason is that the luminescent substrate is luciferin. Currently, luciferin in D form, which is a natural luminescent substrate, is synthesized from D-cysteine, which is a non-natural amino acid. However, D-cysteine is extremely high in cost.

<Needs and Conditions of Long Wavelength Light Using a Bioluminescent System>

In order to measure a variety of phenomena, multicolor light emission is desired also for detection systems that use labeling. Therefore, the wavelength range of labeling material that can be used in a detection system is preferably wide. For example, in the research using multicolor light emission, labeling materials that emit light with a wavelength of approximately 450 nm to 650 nm or more as the label, particularly 680 nm or more, is preferably prepared. For in vivo labeling of deep portions, a red light emission labeling material is preferable since longer wavelength light yields better optical transmittance than shorter wavelength light. In particular, near-infrared light with a wavelength of 650 nm to 900 nm is used for the optical measurement of body tissue. Visible light (400 nm to 700 nm) is greatly absorbed by hemoglobin and other biological substances, whereas at wavelengths longer than near-infrared light, light is increasingly absorbed by water, so that light cannot proceed through the living organism. By contrast, the wavelength region of near-infrared light easily passes through the living organism and is therefore also referred to as a "window into the body".

As described above, the firefly bioluminescence occurs by a chemical reaction between luciferin and luciferase. Using this fact, a luminescent enzyme may be created in advance by genetic engineering in a target organ, for example, and by subsequently dispersing luciferin throughout the body by intravenous administration or by intraperitoneal administration to the individual, the target organ that expresses the luminescent enzyme emits light. Furthermore, if cancer is transplanted to the target organ, the use is possible for visualization of cancer and for the basic research into regenerative medicine if the target organ is an organ from another organism. In particular, if the material is a long wavelength material that emits light in the region of the window into the body, the transmittance in the organism is high, and measurement from outside the organism is considered to be easier.

Currently, substrates with several emission wavelengths can be acquired as luminescent substrates for a firefly bioluminescent system. Examples of the shortest and longest wavelengths of the substrates include coelenterazine blue (approximately 480 nm) and firefly red (approximately 613 nm). Recently, longer wavelength red luminescent material (approximately 630 nm) using a railroad worm luminescent enzyme has become commercially available. Since longer wavelength light yields better optical transmittance, the latent demand is expected to exist for not only these emission wavelengths, but also for further expansion of the longest emission wavelength.

The following are examples of existing products that emit red and blue light using a bioluminescent system.

1. Promega KK: Chroma-Luc: approximately 613 nm (Non-patent Literature 1)

This system uses a mutant click beetle and a native firefly luminescent substrate.

2. TOYOBO Co., Ltd.: MultiReporter Assay System-Tripluc: approximately 630 nm (Non-patent Literature 2)

This system uses a red luminescent enzyme of the railroad worm and a native firefly luminescent substrate. The luminescent color is varied using luciferase genes for the colors of green luminescent luciferase (SLG, maximum emission wavelength of 550 nm), orange luminescent luciferase (SLO, 580 nm) and red luminescent luciferase (SLR, 630 nm). Luminescent enzymes yielding different luminescent colors are used.

3. University of Tokyo: Aminoluciferin: approximately 610 nm (Patent Literature 1)

This discloses a luciferin derivative.

4. Promega KK: Chroma-Luc: approximately 480 nm (Non-patent Literature 3)

This system uses coelenterazine and *Renilla reniformis* luciferase.

5. ATTO Corporation: Vargula hilgendorfii bioluminescence, approximately 460 nm (Non-patent Literature 4)

This system uses a coelenterazine-based substrate and Vargula hilgendorfii luciferase.

The present inventors have also disclosed luciferin analog compounds in Patent Literature 2. These compounds have a similar skeleton to luciferin.

Furthermore, in Patent Literature 4, the present inventors have disclosed luciferin analog compounds that have a different skeleton from luciferin and that have a variety of emission wavelengths. For these luciferin analog compounds as well, there is a desire to shift the emission wavelength to an even longer wavelength.

Patent Literature 1: JP 2007-091695A
Patent Literature 2: WO 2007/116687A
Patent Literature 3: JP 2006-219381A
Patent Literature 4: JP 2010-215795A
Non-patent Literature 1: Promega KK General Catalogue 2008-9, 12.6
Non-patent Literature 2: Upload vol. 79, 2005 pp. 1-10, Toyobo Biochemicals for Lifescience 2006/2007 pp. 4-67
Non-patent Literature 3: Promega KK General Catalogue 2008-9, 12.14
Non-patent Literature 4: ATTO Corporation. General Catalogue 2008-2009, p. 247

SUMMARY OF INVENTION

Technical Problem

The present invention has been conceived in light of the above circumstances, and it is an object thereof to provide a new luminescent substrate for which the emission wavelength in a firefly bioluminescent system is shifted to a longer wavelength than that of a conventional luminescent substrate.

Solution to Problem

In order to achieve the above object, the present inventors produced a group of analogs for a luminescent substrate having a structure similar to luciferin and analyzed the emission wavelengths thereof. As a result, the present inventors discovered that the emission wavelength is shifted to a longer wavelength if the structure of the luciferin and luciferin analog is modified at a particular position.

The present invention provides a compound of general formula I or a salt thereof:

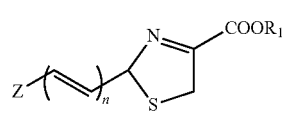

[Chem. 1]

wherein Z is

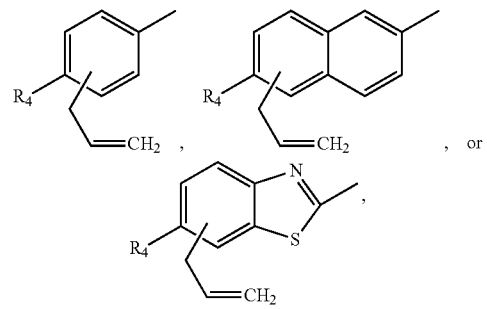

[Chem. 2]

$R_1$ is H or $C_{1-4}$ alkyl,
$R_4$ is OH or $NR_2R_3$, and $R_2$ and $R_3$ are H or $C_{1-4}$ alkyl, and
n is 0, 1, 2, or 3.

The present invention also provides the above compound or a salt thereof, wherein $R_1$, $R_2$, and $R_3$ are H, and $R_4$ is OH.

Furthermore, the present invention provides a luminescent substrate of luciferase including the above compound.

Furthermore, the present invention provides a kit for detecting luminescence including the above compound.

Advantageous Effect of Invention

According to the present invention, luciferin and a luciferin analog that are modified without impairing luminescent activity are provided. In particular, a new luminescent substrate for which the emission wavelength in a firefly bioluminescent system is shifted to a longer wavelength than that of a conventional luminescent substrate is provided according to the present invention.

BRIEF DESCRIPTION OF DRAWINGS

FIG. 1 illustrates the emission wavelength of a modified firefly luciferin according to the present invention; and FIG. 2 illustrates the emission wavelength of a modified firefly luciferin analog according to the present invention.

DESCRIPTION OF EMBODIMENTS

The present invention provides a luciferin analog exhibiting luminescent activity. In the present description, a luciferin analog refers to a substance that emits light by reacting with luciferase or with a luciferase variant. A luciferase variant refers to a luciferase protein for which the substrate characteristics and emission wavelength are varied by, for example, genetically modifying luciferase.

The present invention provides a compound of the general formula below or a salt thereof:

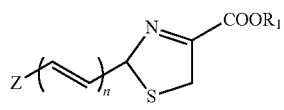

[Chem. 3]

wherein Z is

[Chem. 4]

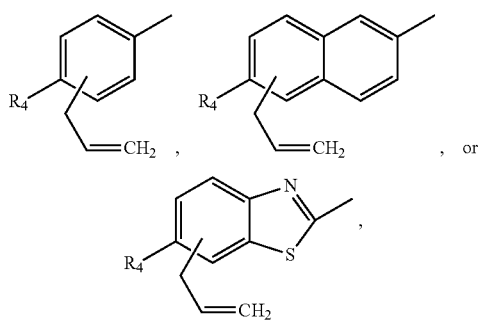

$R_1$ is H or $C_{1-4}$ alkyl, $R_4$ is OH or $NR_2R_3$, and $R_2$ and $R_3$ are H or $C_{1-4}$ alkyl, and n is 0, 1, 2, or 3. In particular, in the above compound, $R_1$, $R_2$, and $R_3$ may be H, and $R_4$ may be OH.

Furthermore, in the above compound, the compound recited as a Markush expression in the benzene ring indicates that the binding site is arbitrary, yet in the compound according to the present invention, Z may be any of the following compounds:

[Chem. 5]

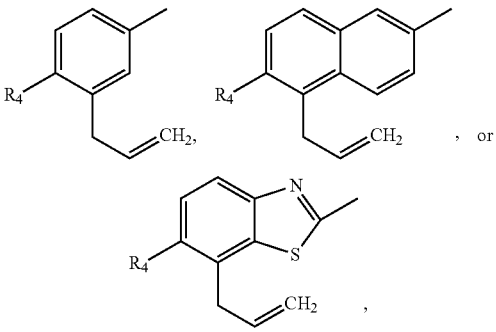

wherein $R_4$ is OH or $NR_2R_3$, and $R_2$ and $R_3$ are H or $C_{1-4}$ alkyl.

In a specific embodiment, the present invention provides a firefly luciferin analog in which the benzothiazole moiety that has been modified at the 7-position with an allyl group. In the present disclosure, luciferin has the following structure.

[Chem. 6]

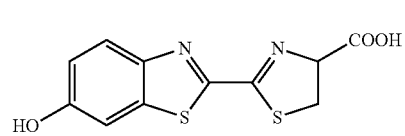

The firefly luciferin analog may be modified. In the present disclosure, the modification refers to binding any group to any compound. The modification site may be the site corresponding to the 7-position of the benzothiazole moiety. For example, a compound with general formula I below is possible:

[Chem. 7]

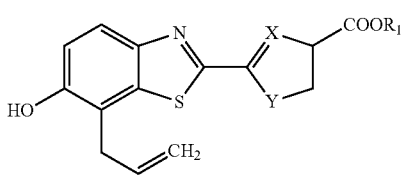

wherein $R_1$ is H or $C_{1-4}$ alkyl, and

X and Y independently represent C, N, S, or O.

In the present disclosure, the term "$C_{1-4}$ alkyl" refers to a saturated straight-chain or branched-chain alkyl group that includes 1 to 4 carbon atoms, such as methyl, ethyl, n-propyl, iso-propyl, n-butyl, iso-butyl, sec-butyl, and tert-butyl. Similarly, the term "$C_1$-$C_3$ alkyl" refers to a saturated straight-chain or branched-chain alkyl group that includes 1 to 3 carbon atoms (such as methyl, ethyl, or iso-propyl).

A person of ordinary skill in the art would easily understand that $R_1$ may be a $C_{1-4}$ alkyl as above. For example, in Patent Literature 2, the present inventors have disclosed the result that a luciferin analog compound in which the moiety corresponding to the $R_1$ moiety of the compound according to the present invention is AMP can become a substrate for a firefly bioluminescent system. Accordingly, as a substituent, it is considered that such a low-level alkyl is not likely to affect activity.

In the above general formula I, X and Y may independently represent C, N, S, or O. A person of ordinary skill in the art would easily understand that the heteroatom in X and Y may be C, N, S, or O. For example, in Patent Literature 2, the present inventors have disclosed the result that, among the variety of disclosed luciferin analog compounds, a luciferin analog compound in which a moiety, corresponding to the compound according to the present invention, is a variety of heteroatoms can become a substrate for a firefly bioluminescent system.

In one embodiment, the present invention provides the following compound, in which in general formula I, $R_1$ is H, X is N, and Y is S:

[Chem. 8]

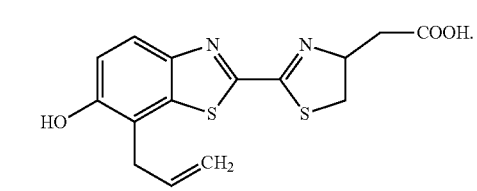

The compound with the above formula emits light having an emission wavelength of approximately 605 nm by reacting with firefly luciferase.

As another specific embodiment, the present invention provides the compound of general formula II below:

[Chem. 9]

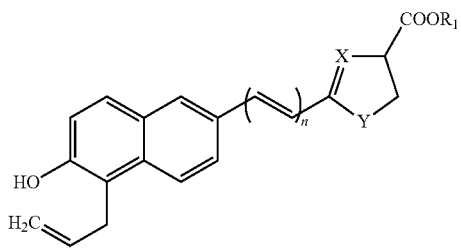

wherein
$R_1$ is H or $C_{1-4}$ alkyl,
X and Y independently represent C, N, S, or O, and
n is 0, 1, 2, or 3.

A person of ordinary skill in the art would easily understand that $R_1$ may be $C_{1-4}$ alkyl in general formula II as above.

In general formula II, X and Y may independently represent C, N, S, or O as above. A person of ordinary skill in the art would easily understand that the heteroatom in X and Y may be C, N, S, or O.

A person of ordinary skill in the art would easily understand that, as above, in general formula II, the olefin chain unit represented by "n" can be changed to a desired length.

In a specific embodiment, the present invention provides the following compound, in which in general formula II, $R_1$ is H, X is N, Y is S, and n is 1:

[Chem. 10]

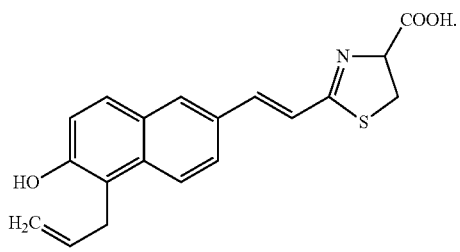

The compound with the above formula emits light having an emission wavelength of approximately 690 nm by reacting with firefly luciferase.

As another specific embodiment, the present invention provides the compound of general formula III below:

[Chem. 11]

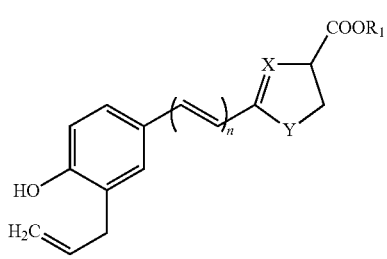

wherein
each $R_1$ independently represents H or $C_{1-4}$ alkyl,
X and Y independently represent C, N, S, or O, and
n is 0, 1, 2, or 3.

A person of ordinary skill in the art would easily understand that $R_1$ may be $C_{1-4}$ alkyl in general formula III as above.

X and Y may independently represent C, N, S, or O in general formula III as above. A person of ordinary skill in the art would easily understand that the heteroatom in X and Y may be C, N, S, or O.

A person of ordinary skill in the art would easily understand that, as above, in general formula III, the olefin chain unit represented by "n" can be changed to a desired length.

In general formula I, general formula II, and general formula III, the —OH group may be substituted with a —$NR_2R_3$ group. In the —$NR_2R_3$ group, $R_2$ and $R_3$ may independently represent H or $C_{1-4}$ alkyl.

A person of ordinary skill in the art would easily understand that $R_2$ and $R_3$ may be $C_{1-4}$ alkyl as above. For example, in Patent Literature 4, the present inventors have disclosed the result that a luciferin analog compound in which the moiety corresponding to the —OH group of the compound according to the present invention is a —$N(CH_3)_2$ group can become a substrate for a firefly bioluminescent system. Accordingly, as a substituent, it is considered that such a $NR_2R_3$ group is not likely to affect activity.

In the present invention, the modified luciferin and modified luciferin analog include salts thereof. A "salt" is only envisioned for the case in which some moiety of the compound according to the present invention forms a base.

The expression "salt" includes any salts of hydrochloric acid, hydrobromic acid, hydroiodic acid, sulfuric acid, sulfamic acid, phosphoric acid, nitric acid, phosphorous acid, nitrous acid, citric acid, formic acid, acetic acid, oxalic acid, maleic acid, lactic acid, tartaric acid, fumaric acid, benzoic acid, mandelic acid, cinnamic acid, pamoic acid, stearic acid, glutamic acid, aspartic acid, methane sulfonic acid, ethane disulfonic acid, p-toluene sulfonic acid, salicylic acid, succinic acid, trifluoroacetic acid, and any other inorganic acids or organic acids that are non-toxic for a living organism, as well as salts with an inorganic base such as an alkali or an alkaline earth base, for example sodium hydroxide, potassium hydroxide, calcium hydroxide, and the like, when the compound of formula I is acidic.

The modified luciferin and modified luciferin analog of the present invention may, for example, be manufactured in accordance with the procedure listed in the Examples below. While a more detailed procedure is listed in the Examples below, the compound of general formula I may, for example, be manufactured in accordance with the procedure below.

[Chem. 12]

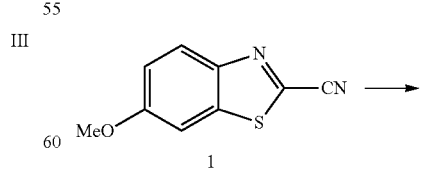

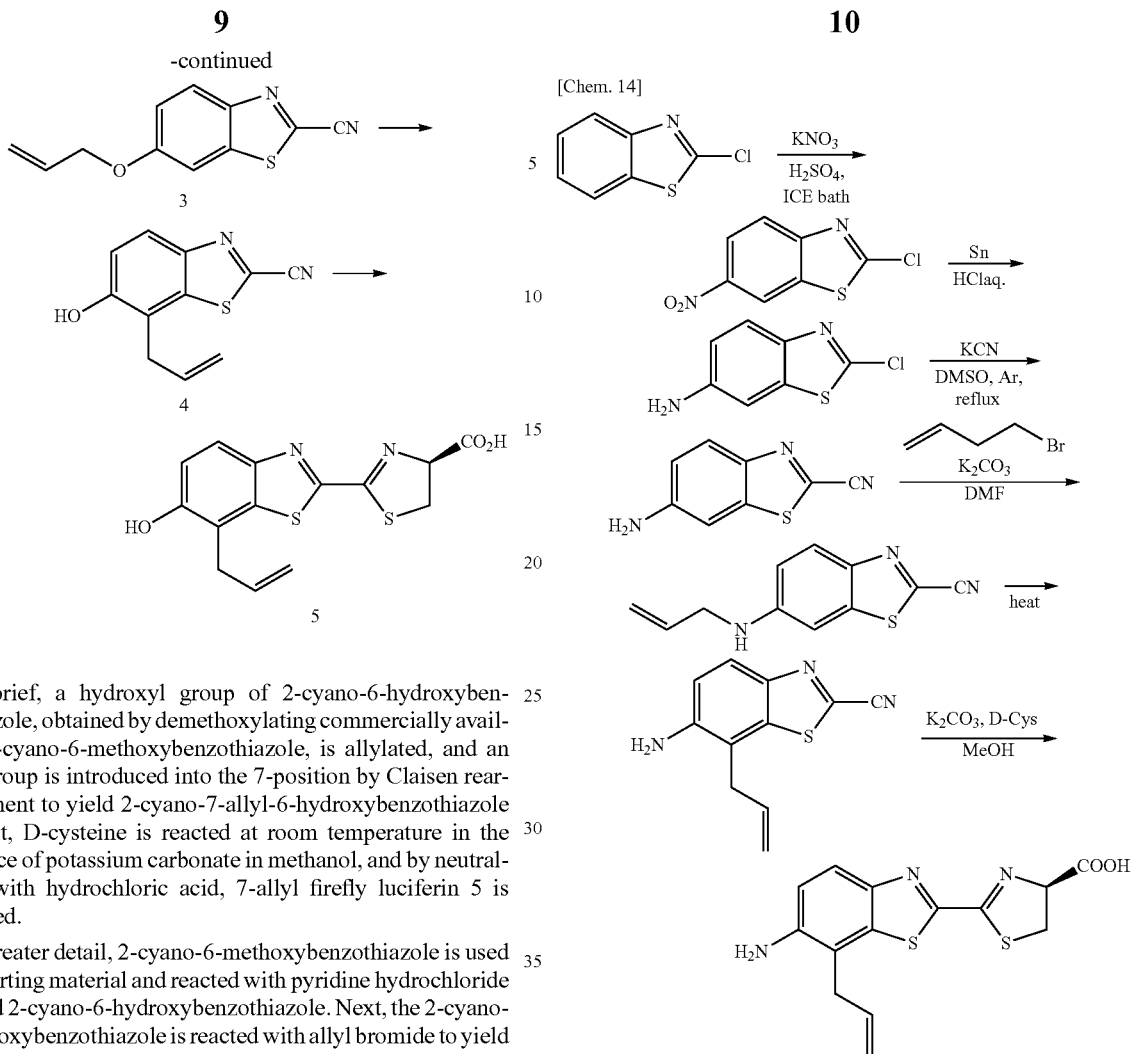

In brief, a hydroxyl group of 2-cyano-6-hydroxybenzothiazole, obtained by demethoxylating commercially available 2-cyano-6-methoxybenzothiazole, is allylated, and an allyl group is introduced into the 7-position by Claisen rearrangement to yield 2-cyano-7-allyl-6-hydroxybenzothiazole 4. Next, D-cysteine is reacted at room temperature in the presence of potassium carbonate in methanol, and by neutralizing with hydrochloric acid, 7-allyl firefly luciferin 5 is obtained.

In greater detail, 2-cyano-6-methoxybenzothiazole is used as a starting material and reacted with pyridine hydrochloride to yield 2-cyano-6-hydroxybenzothiazole. Next, the 2-cyano-6-hydroxybenzothiazole is reacted with allyl bromide to yield 6-allyloxy-benzothiazole-2-carbonitrile.

The resulting 6-allyloxy-benzothiazole-2-carbonitrile is melted by heating at 180° C. in an argon atmosphere, and after allowing the reaction mixture to cool, 7-allyl-6-hydroxybenzothiazole-2-carbonitrile is obtained. Next, the 7-allyl-6-hydroxybenzothiazole-2-carbonitrile is melted by heating at 180° C. in an argon atmosphere to obtain 7-allyl-6-hydroxybenzothiazole-2-carbonitrile. Next, 2-cyano-7-allyl-6-hydroxybenzothiazole and D-cysteine hydrochloride monohydrate are dissolved in methanol:distilled water, and by adding potassium carbonate in an argon atmosphere, 7-allyl-firefly luciferin can be obtained.

The compound of the following general formula:

[Chem. 13]

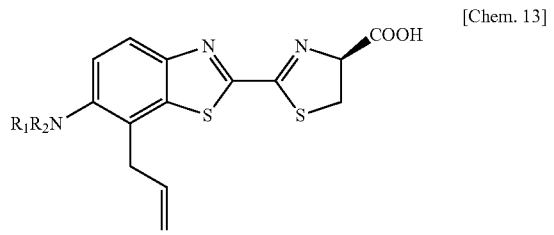

may, for example, be manufactured in accordance with the following procedure.

By adding potassium nitrate under ice cooling in concentrated sulfuric acid to commercially available 2-chlorobenzothiazole and nitrating, and then reacting the generated 2-chloro-6-nitrobenzothiazole with tin in hydrochloric acid, the nitro group is reduced to an amino group, thus deriving 2-chloro-6-aminobenzothiazole. Adding potassium cyanide thereto in an argon atmosphere in DMSO solvent and heating to reflux overnight yields 2-cyano-6-aminobenzothiazole. Allyl bromide and potassium carbonate are reacted in DMF solvent to allylate the amino group, and by aza-Claisen rearrangement, an allyl group is introduced into the 7-position. Potassium carbonate in methanol and cysteine are added and stirred, and by neutralizing with hydrochloric acid, a 7-allyl-aminoluciferin-type compound can be obtained.

A person of ordinary skill in the art will understand that starting with starting material in which a substituent group of the compound in general formula I above is substituted with a desired substituent group, a corresponding compound can be synthesized with a similar procedure to the above synthesis procedure. A person of ordinary skill in the art will also understand that in an appropriate step of the above synthesis procedure, a substituent group of the compound may be substituted with a desired substituent group. In the last step, by substituting a desired ester for the carboxylic acid moiety, a compound having the corresponding $R_1$ could also be obtained.

While a more detailed procedure is listed in the Examples below, the compound of general formula II may, for example, be manufactured in accordance with the procedure below.

[Chem. 15]

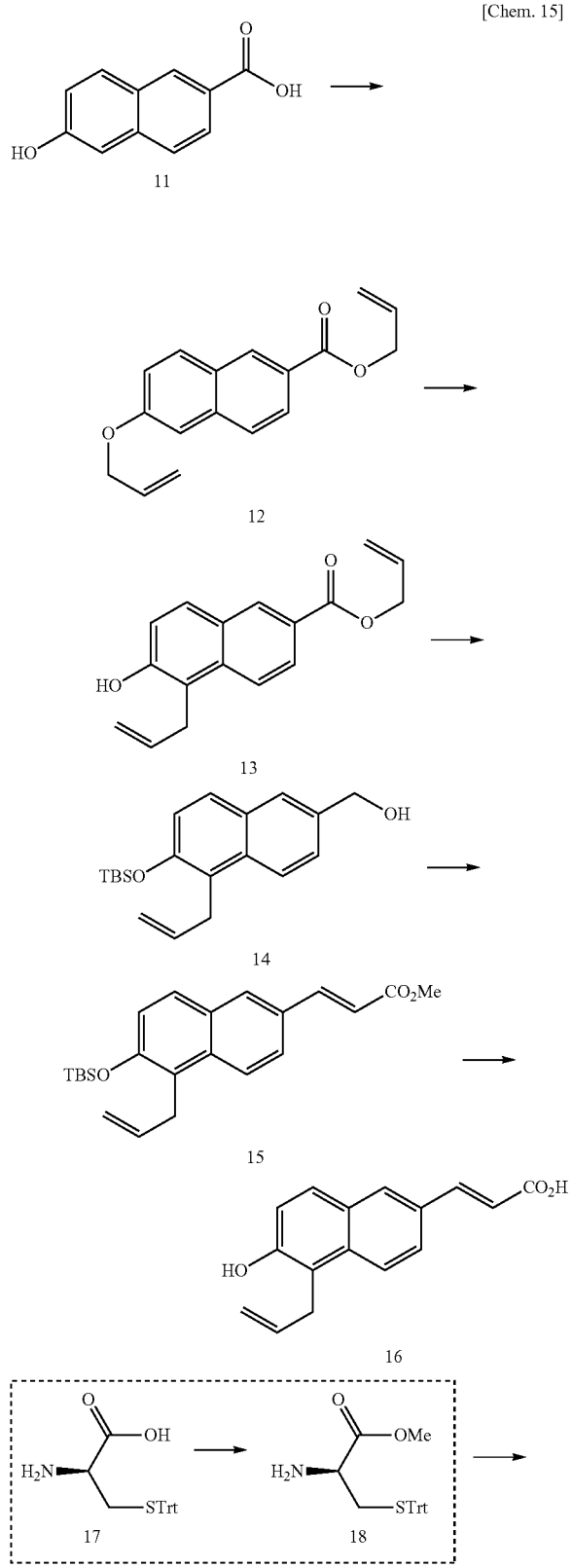

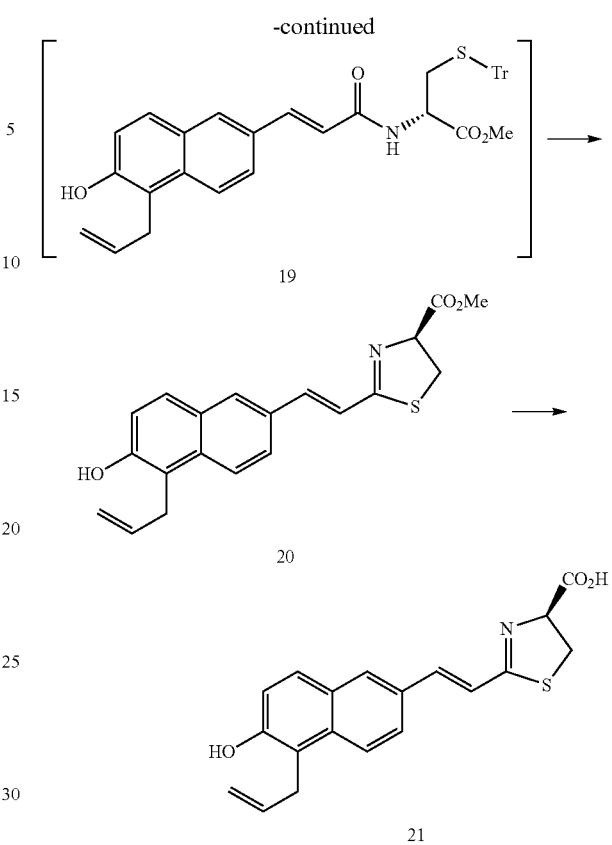

In brief, a diallyl product 12 is obtained by diallylating commercially available hydroxynaphthoic acid 11. By introducing an allyl group into an aromatic ring by Claisen rearrangement and reducing the ester moiety to hydroxymethylene with DIBAL-H, 14 is obtained. By oxidation and by homologization via a Wittig reaction, compound 15 is obtained. By similarly repeating reduction and homologization, the number of double bond sites can be increased to a desired number. The ester moiety is made into a carboxyl group by hydrolysis, an amide bond is formed with a D-cysteine derivative, and the result is cyclized to obtain compound 20. Using esterase or lipase, the ester moiety can be hydrolyzed to obtain compound II.

In greater detail, 2-naphthoic acid is dissolved in acetone and reacted with potassium carbonate and allyl bromide under ice cooling to obtain compound 2. Compound 2 is heated at 200° C. to obtain compound 3.

Next, compound 3 is dissolved in tetrahydrofuran, reacted with t-butyldimethylsilyl chloride and triethylamine at room temperature and then further reacted with diisobutylaluminium hydride at −78° C. to obtain compound 14.

Next, compound 14 is dissolved in dichloromethane and reacted with manganese oxide at room temperature, and the product is further dissolved in benzene and reacted with (carbomethoxymethylene) triphenylphosphorane at room temperature to obtain compound 15. Next, compound 15 is dissolved in isopropyl alcohol and reacted with 1M aqueous sodium hydroxide to obtain compound 16.

Meanwhile, a D-cysteine-5-trityl compound is dissolved in methanol and reacted with a 1,4-dioxane solution of 4 N hydrogen chloride to obtain compound 18.

Next, compound 16 and compound 18 are dissolved in pyridine and reacted with hydrochloric acid 1-ethyl-3-(3- dimethylaminopropyl) carbodiimide and 1-hydroxybenzotriazole to obtain compound 19. Next, compound 19 is dissolved in dichloromethane and reacted with triphenylphosphine oxide and anhydrous trifluoromethanesulfonic acid at 0° C. to obtain compound 20.

Finally, compound 20 is dissolved in tetrahydrofuran, ethanol, and a 10 m ammonium carbonate aqueous solution and reacted with porcine pancreas lipase at 40° C. to obtain compound 21.

The compound of the following general formula:

[Chem. 16]

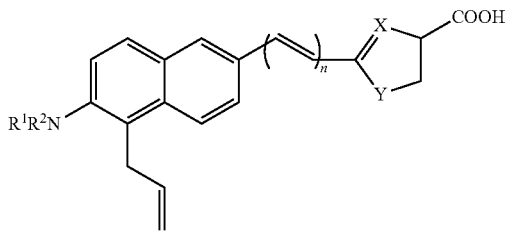

may, for example, be manufactured in accordance with the following procedure. An amino group of commercially available 6-aminonaphthylaldehyde is allylated, and an allyl group is introduced into the 7-position by aza-Claisen rearrangement. By homologization via a Wittig reaction, an α,β-unsaturated ester product is obtained. By repeating reduction and homologization of the ester moiety, the number of double bond sites (n) can be increased to a desired number. The amino group is dialkylated, the ester moiety is made into a carboxyl group by hydrolysis, an amide bond is formed with a D-cysteine derivative, and the result is cyclized to obtain an ester product. Using esterase or lipase, the ester moiety can be hydrolyzed to obtain a 7-allyl-dimethylaminonaphthol-type compound. With similar steps, if the amino group is not alkylated, a 4-amino type (—NH$_2$) 7-allyl-aminonaphthol-type compound in which R$_1$=R$_2$=H can be obtained. Furthermore, a 7-allyl-aminonaphthol-type compound can be obtained by using 4-nitronaphthylaldehyde as a starting material, reducing the nitro group to an amino group, and performing a similar reaction.

A person of ordinary skill in the art will understand that starting with starting material in which a substituent group of the compound in general formula II above is substituted with a desired substituent group, a corresponding compound can be synthesized with a similar procedure to the above synthesis procedure. A person of ordinary skill in the art will also understand that in an appropriate step of the above synthesis procedure, a substituent group of the compound may be substituted with a desired substituent group. In the last step, by substituting a desired ester for the methyl ester moiety, a compound having the corresponding R$_1$ could also be obtained. Furthermore, by changing the length of the olefin moiety in the compound used as the starting material, a compound with a desired length for "n" in general formula II could be obtained.

A person of ordinary skill in the art will understand that starting with starting material in which the compound in general formula II above is substituted with a desired skeleton and substituent group, a corresponding compound III can be synthesized with a similar procedure to the above synthesis procedure. A person of ordinary skill in the art will also understand that in an appropriate step of the above synthesis procedure, a substituent group of the compound may be substituted with a desired substituent group. In the last step, by substituting a desired ester for the methyl ester moiety, a compound having the corresponding R$_1$ could also be obtained. Furthermore, by changing the length of the olefin moiety in the compound used as the starting material, a compound with a desired length for "n" in general formula III could be obtained.

For example, a hydroxyl group of commercially available 4-hydroxybenzaldehyde is allylated, and an allyl group is introduced into the 3-position by aza-Claisen rearrangement. By homologization via a Wittig reaction, an α,β-unsaturated ester product is obtained. By repeating reduction and homologization of the ester moiety, the number of double bond sites can be increased to a desired number. The ester moiety is made into a carboxyl group by hydrolysis, an amide bond is formed with a D-cysteine derivative, and the result is cyclized to obtain an ester product. Using esterase or lipase, the ester moiety can be hydrolyzed to obtain compound III. If 4-aminobenzaldehyde is used instead of 4-hydroxybenzaldehyde as the starting material, with similar steps, a 4-amino type (—NH$_2$) compound in which R$_1$=R$_2$=H can be obtained. Furthermore, using a similar reaction to the reaction for obtaining compound 10 above, cyclization can be performed. Using a similar reaction to the reaction for obtaining compound 11, hydrolysis of a compound can be performed.

The compound of the following general formula:

[Chem. 17]

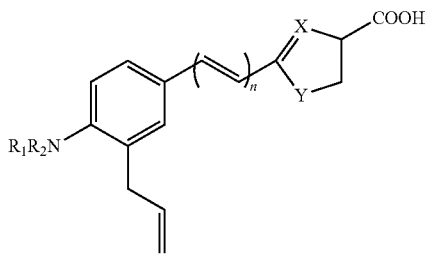

may, for example, be manufactured in accordance with the following procedure. An amino group of commercially available 4-dimethylaminobenzaldehyde is allylated, and an allyl group is introduced into the 3-position by aza-Claisen rearrangement. By homologization via a Wittig reaction, an α,β-unsaturated ester product is obtained. By repeating reduction and homologization of the ester moiety, the number of double bond sites (n) can be increased to a desired number. The ester moiety is made into a carboxyl group by hydrolysis, an amide bond is formed with a D-cysteine derivative, and the result is cyclized to obtain an ester product. Using esterase or lipase, the ester moiety can be hydrolyzed to obtain a 3-allyl-dimethylaminodiene-type compound. If 4-aminobenzaldehyde is used instead of 4-dimethylaminobenzaldehyde as the starting material, with similar steps, a 4-amino type (—NH$_2$) compound in which R$_1$=R$_2$=H can be obtained. A 3-allyl-dimethylaminodiene-type compound can also be obtained by using 4-nitrobenzaldehyde as a starting material, reducing the nitro group to an amino group, and performing a similar reaction.

Furthermore, in accordance with the procedure disclosed in JP 2010-180191A, a luciferin and luciferin analog can be modified with an allyl group at the 7-position of the benzothiazole ring moiety, the 6-position of the phenol moiety, and the 5-position of the naphthol moiety.

By being added to a system in which luminescent beetle luciferase, ATP, and $Mg^{2+}$ are present, the compound according to the present invention emits light by oxidation due to the luminescent beetle luciferase. The compound according to the present invention may be used independently as a luminescent substrate, or as necessary, may be used in combination with another luminescent substrate. The compound according to the present invention can be provided in a kit along with ATP and $Mg^{2+}$. Another luminescent substrate or a solution adjusted to an appropriate pH can be included in the kit. Furthermore, the compound according to the present invention can be provided in a luminescent agent kit with a luminescent substrate composition in which the compound according to the present invention is adjusted to an appropriate pH along with ATP and $Mg^{2+}$.

Since the firefly bioluminescent system is an aqueous system, a hydrophilic organic compound may be present. For example, tetrafluoroacetic acid, acetic acid, formic acid, and the like may be present. When the compound according to the present invention is applied to a luminescent system, use at a concentration of the luminescent substrate of 1 μM or more is preferable in order to achieve suitable emission intensity. The compound is used, for example, at 5 μM or more. Furthermore, the pH of the luminescent system is assumed to be 4 to 10, and preferably 6 to 8, yet is not particularly limited. As necessary, buffers such as potassium phosphate, tris hydrochloric acid, glycine, HEPES, and the like can be used in order to stabilize the pH.

In a firefly luminescent beetle luciferase luminescent system, the compound according to the present invention can be caused to emit light by a variety of oxidases. Luciferase has been isolated from a variety of organisms, such as the North American firefly (*Photinus pyralis*) and the railroad worm, and any of these may be used. Oxidases that can be used include, for example, click beetle luciferase, *Rhagophthalmus ohbai* luciferase, and flavin-containing monooxygenase.

For the bioluminescence using the compound according to the present invention as the luminescent substrate, it is known that if coenzyme A (CoA), pyrophosphoric acid, or magnesium ions ($Mg^{2+}$) are present in the luminescent system, the emitted light is enhanced. Therefore, these may be used as a luminescence enhancer for a luminescent beetle luciferase luminescent system. It is known that the luminescence enhancement effect of these compounds is remarkable when the concentration of CoA, pyrophosphoric acid, or $Mg^{2+}$ is 5 μM or more, and that the enhancement increases as the concentration rises.

In order to use the firefly bioluminescent system for measurement/detection, it is important to stabilize light emission so as to prevent deactivation of the enzyme and to achieve plateaued luminescence behavior. For example, Mg ions are effective for stabilization of light emission in the firefly bioluminescent system. If Mg ions are present in the luminescent system, the luminescence behavior changes so that attenuation after rising is suppressed. In particular, if both pyrophosphoric acid and Mg ions are present in the luminescent system, the luminescence behavior changes greatly. In other words, stabilization of light emission becomes particularly remarkable, and when a great excess of pyrophosphoric acid and Mg ions coexist with the luminescent substrate, the luminescence behavior is such that after a rapid rise, light emission is maintained in a plateau state. In the case of Mg ions alone, the light emission stabilization effect is remarkable at an Mg ion concentration of 0.5 mM or more in the luminescent system and is enhanced as the concentration of Mg ions increases. In order to achieve plateaued luminescence behavior, for example magnesium pyrophosphate at a concentration of 10 μM or more, preferably 100 μM or more, can be included. The ratio between pyrophosphoric acid and Mg ions need not be an equivalent ratio. While magnesium pyrophosphate is not very soluble in water, using magnesium pyrophosphate allows for pyrophosphoric acid and Mg ions to be supplied separately. These can be supplied to the luminescent system in free form and in salt form. Mg salts that can be used include inorganic acid salts such as magnesium sulfate and magnesium chloride, as well as organic acid salts such as magnesium acetate. Pyrophosphate includes salts with an alkali metal, such as sodium and potassium, as well as salts with an alkaline earth metal, such as magnesium and calcium, and salts with iron and the like. These salts may be included in the luminescent system in aqueous solution form. Furthermore, considering the effect on enzymes, salts are preferably included so that the pH of the luminescent system is from 2 to 10.

The compound according to the present invention may be used as a substrate in chemiluminescence. Chemiluminescence is produced by the compound according to the present invention being oxidized to generate a peroxide, and a degradation product of the peroxide becoming a luminescent species in an excited state. Oxidation can be caused to progress by air oxidation using, for example, t-butoxypotassium in DMSO. In the case of chemiluminescence, light emitted at a shorter wavelength than the light emitted with a firefly bioluminescent system is assumed.

The compound according to the present invention can be used for luminescent labeling in biological measurement/detection. For example, the compound can be used for labeling amino acids, polypeptides, proteins, nucleic acids, and the like. A person of ordinary skill in the art is well aware of a means for binding the compound according to the present invention to these substances. For example, using a method well known to a person of ordinary skill in the art, the compound according to the present invention can be bound to the carboxyl group and amino group of the target substance.

The compound according to the present invention can also be used for measurement/detection that takes advantages of detection of luminescent beetle luciferase activity via light emission of a luminescent substrate. For example, the compound according to the present invention is reacted under conditions suitable for reaction with a luminescent beetle luciferase as described above. Next, the light emission from the compound is detected. For example, by administering the compound according to the present invention to a cell or an animal into which a luciferase gene has been introduced, measurement/detection of expression or the like of the target gene or protein in vivo is possible. Compounds according to the present invention can be caused to emit light with different emission wavelengths. Therefore, by using a plurality of compounds, light emission by a plurality of targets can be measured/detected simultaneously.

Since the optical transmittance is higher as the wavelength of light increases, tissue permeability is also high. Therefore, as compared to a luciferin and luciferin analog not modified with an allyl group, a luciferin and luciferin analog modified with an allyl group according to the present invention emit a longer wavelength of light. In particular, by modifying a luciferin and luciferin analog with an allyl group at the 7-position of the benzothiazole ring moiety, the 6-position of the phenol moiety, and the 5-position of the naphthol moiety, the emission wavelength can be shifted to a longer wavelength. Hence, the luciferin and luciferin analog modified with an allyl group are useful for in vivo labeling of deep portions in an organism.

EXAMPLES

In the following examples, the present invention is described concretely, yet the present invention is not limited in scope to these examples.

1) Instrumental Analysis and Measurement Device pH measurement: pH was measured using pH measurement paper UNIV produced by Toyo Roshi Kaisha, Ltd. Measurement was performed using a pH/ION METER F-23 produced by HORIBA, Ltd. for the pH meter.

$^1$H nuclear magnetic resonance spectrum ($^1$H NMR): measured using a Lambda-270 type device (270 MHz) produced by JEOL Ltd. Measurements are listed as "$^1$H NMR (measuring frequency, measuring solvent): δ chemical shift value (number of hydrogens, multiplicity, spin coupling constant)". The chemical shift value (δ) is listed in ppm, with tetramethylsilane (δ=0) as an internal reference. Multiplicity is indicated as s (single), d (doublet), t (triplet), q (quadruplet), or m (multiplet or complex overlapping signals), and a broad signal is listed as br. The spin coupling constant (J) is listed in Hz.

$^{13}$C nuclear magnetic resonance spectrum ($^{13}$C NMR): measured using a Lambda-270 type device (67.8 MHz) produced by JEOL Ltd. Measurements are listed as "$^{13}$C NMR (measuring frequency, measuring solvent): δ chemical shift value (multiplicity)". The chemical shift value (δ) is listed in ppm, with tetramethylsilane (δ=0) as an internal reference. Multiplicity is indicated as s (single), d (doublet), t (triplet), or q (quadruplet).

Mass spectrum (MS): measured using a JMS-600H type mass spectrometer produced by JEOL Ltd., with an electron impact method (EI, ionization energy: 70 eV). Measurement was performed using a JMS-T100LC type TOF mass spectrometer AccuTOF, produced by JEOL Ltd., with electrospray ionization (ESI). Note that the device settings were desolvation gas 250° C., orifice 1 temperature 80° C., needle voltage 2000 V, ring lens voltage 10 V, orifice 1 voltage 85 V, and orifice 2 voltage 5 V. The sample was sent by infusion, with a flow rate of 10 μl/min. Measurements are listed as "MS (measurement method) m/z mass number (relative intensity)".

Specific optical rotation: measured using a DIP-1000 type polarimeter produced by JASCO Corporation. A sodium lamp was used as the light source, and a cylindrical glass cell (4) 10 mm×100 mm) was used as the cell. The measurement values are unadjusted values, and the data are the average of five measurements. D and L products are listed as "D or L: [α] temperature measurement value (concentration, measuring solvent)".

2) Chromatography

Analytical thin layer chromatography (TLC): TLC plates produced by E. Merck KG, silica gel 60F$_{254}$ (Art. 5715), thickness 0.25 mm were used. The compound on the TLC was detected by heating and color development after UV irradiation (254 nm or 365 nm) and soaking in a color-producing reagent. The result of dissolving p-anisaldehyde (9.3 ml) and acetic acid (3.8 ml) in ethanol (340 ml) and adding concentrated sulfuric acid (12.5 ml) was used as the color-producing reagent.

Preparative thin layer chromatography (PTLC): performed using either TLC plates produced by E. Merck KG, silica gel 60F$_{254}$ (Art. 5744), thickness 0.5 mm, or 20 cm×20 cm glass plates, onto which silica gel 60GF$_{254}$ (Art. 7730) for thin layer chromatography produced by E. Merck KG was applied, and which were adjusted to a thickness of 1.75 mm.

Silica gel column chromatography: performed using silica gel 60F$_{254}$ (Art. 7734) produced by E. Merck KG.

3) Basic Operation

The reaction solution was cooled by soaking the reaction vessel in a Dewar flask filled with a refrigerant. For room temperature to 4° C., ice water was used as the refrigerant, and for 4° C. to −90° C., liquid nitrogen-acetone was used. The extracted solution after the reaction was dried by cleaning with a saturated sodium chloride solution and then adding anhydrous sodium sulfate or anhydrous magnesium sulfate. When neutralizing with resin after the reaction, cation-exchange resin Amberlite IR120B NA or cation-exchange resin Amberlite IRA4000H AG produced by Organo Corporation was used. Concentration in vacuo of the solution was performed using a rotary evaporator under reduced pressure (20 mmHg to 30 mmHg) in an aspirator. Trace amounts of the solvent were removed using a vacuum pump (approximately 1 mmHg) equipped with a trap cooled in a liquid nitrogen bath. The mixing ratio of each solvent was expressed as a volume ratio.

4) Solvent

For the distilled water, water that was distilled using a GS-200 type distilled water manufacturing device, produced by Advantec Toyo Kaisha, Ltd., and subjected to ion exchange treatment was used.

Toluene, methanol, ethanol, isopropanol, dichloromethane, tetrahydrofuran, N,N-dimethylformamide, and 2-butanone were used by drying a dehydration solvent for organic synthesis or a special grade solvent produced by Kanto Chemical Co., Inc. using a molecular sieve (4A).

The following were used directly as solvents for NMR measurement. CDCl$_3$: produced by ISOTEC Inc., 99.7 ATOM % D, 0.03% TMS; CD$_3$OD: produced by ISOTEC Inc., 99.8 ATOM % D (approximately 0.7 ATOM % $^{13}$C), 0.05% TMS.

Example 1

Synthesis of 7-Allyl-Firefly Luciferin 7-allyl-firefly luciferin was synthesized in accordance with the following synthesis scheme.

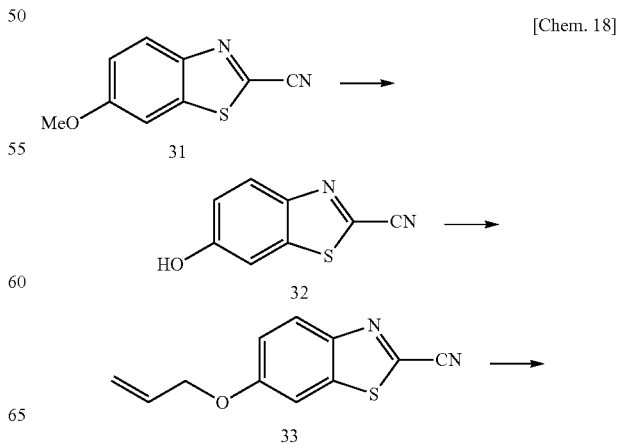

[Chem. 18]

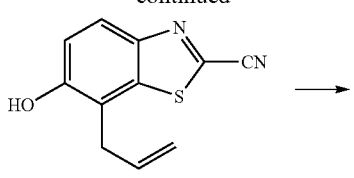

34

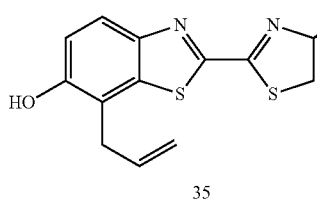

35

Synthesis of 2-Cyano-6-Hydroxybenzothiazole 32

[Chem. 19]

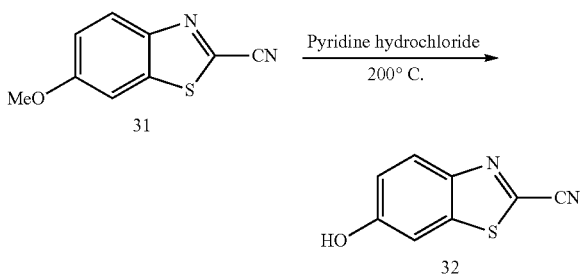

Pyridine hydrochloride (2.32 g) was added to 2-cyano-6-methoxybenzothiazole 31 (51.4 mg, 0.271 mmol) and heated to 200° C. in an argon atmosphere to dissolve the pyridine hydrochloride, and the reaction mixture was stirred for 30 minutes. The reaction mixture was allowed to cool, and then 1 M hydrochloric acid (50 ml) was added. After extraction with ethyl acetate (3×50 ml) and drying of the organic layer with anhydrous sodium sulfate, the result was concentrated in vacuo. The resulting residue was purified by preparative thin-layer silica gel chromatography {one 20 cm×20 cm×1.75 mm plate; hexane-ethyl acetate (1:1)}, yielding 2-cyano-6-hydroxybenzothiazole 32 (47.2 mg, 99%) as a pale yellow solid.

$^1$H NMR (270 MHz, CD$_3$OD) δ 7.17 (1H, dd, J=2.7, 9.2 Hz), 7.41 (1H, d, J=2.7 Hz), 7.99 (1H, d, J=9.2 Hz)

Synthesis of 6-Allyloxy-Benzothiazole-2-Carbonitrile 33

[Chem. 20]

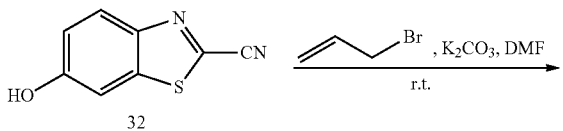

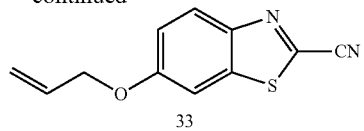

33

2-cyano-6-hydroxybenzothiazole 32 (336.2 mg, 1.91 mmol) and allyl bromide (331 μl, 3.82 mmol) were dissolved in N,N-dimethylformamide (1.5 ml), potassium carbonate (404.6 mg, 1.53 mmol) was added in an argon atmosphere, and the reaction mixture was stirred for an hour at room temperature. Water (20 ml) was added to the reaction mixture, and after extraction with ethyl acetate (3×50 ml) and drying of the organic layer with anhydrous sodium sulfate, the result was concentrated in vacuo. The resulting residue was purified by preparative thin-layer silica gel column chromatography {one 20 cm×20 cm×1.75 mm plate; hexane-ethyl acetate (1:1)}, yielding 6-allyloxy-benzothiazole-2-carbonitrile 33 (418.1 mg, 90%) as a pale yellow solid.

$^1$H NMR (270 MHz, CDCl$_3$) δ 8.07 (1H, d, J=9.2 Hz), 7.36 (1H, d, J=2.4 Hz), 7.26 (1H, dd, J=2.4, 9.2 Hz), 6.08 (1H, m), 5.41 (comp. 2H, m)

Synthesis of 7-Allyl-6-Hydroxybenzothiazole-2-Carbonitrile 34

[Chem. 21]

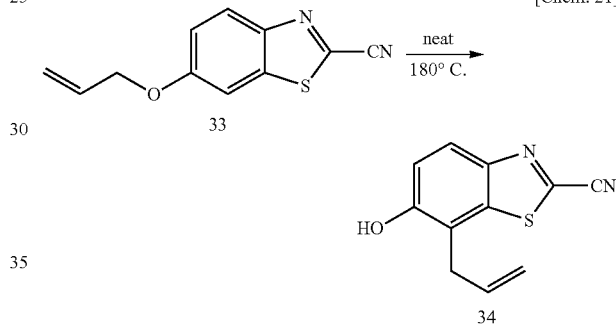

6-allyloxy-benzothiazole-2-carbonitrile 33 (201.0 mg, 0.93 mmol) was melted by heating at 180° C. in an argon atmosphere and stirred for 1 hour. After allowing the reaction mixture to cool, the resulting residue was purified by preparative thin-layer silica gel chromatography {one 20 cm×20 cm×1.75 mm plate; hexane-ethyl acetate (1:1)}, yielding 7-allyl-6-hydroxybenzothiazole-2-carbonitrile 34 (100.0 mg, 50%) as a pale yellow solid.

$^1$H NMR (270 MHz, CDCl$_3$) δ 7.98 (1H, d, J=8.9 Hz), 7.17 (1H, d, J=2.7 Hz), 5.97 (1H, m), 5.74 (1H, s), 5.17-5.25 (comp. 2H), 3.65 (1H, dt, J=1.3, 6.2 Hz)

Synthesis of 7-Allyl-Firefly Luciferin 35

[Chem. 22]

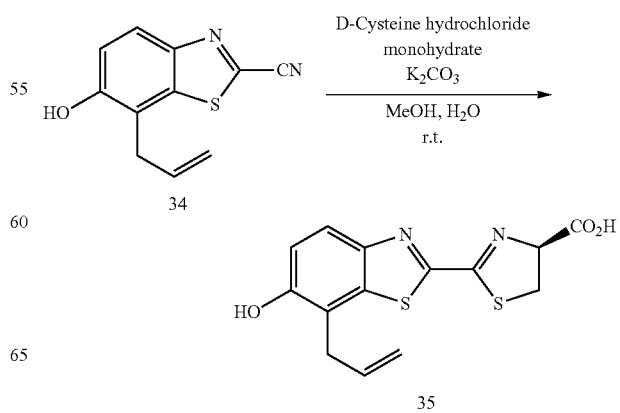

2-cyano-7-allyl-6-hydroxybenzothiazole 34 (50 mg, 0.23 mmol) and D-cysteine hydrochloride monohydrate (45 mg, 0.25 mmol) were dissolved in methanol:distilled water (2:1.6 ml). Potassium carbonate (50 mg, 0.36 mmol) was added in an argon atmosphere, and the result was stirred at room temperature for 40 minutes. The resulting solid was filtered and cleaned with distilled water, yielding 7-allyl-firefly luciferin 35 (64 mg, 84%) as a yellow solid.

$^1$H NMR (270 MHz, CD$_3$OD) δ 7.78 (1H, d, J=8.9 Hz), 7.10 (1H, dd, J=8.9 Hz), 5.92 (1H, m), 5.42 (1H, t, J=8.9 Hz), 5.15-5.03 (comp. 2H), 3.75 (2H, d, J=8.1 Hz), 3.59 (2H, J=6.2 Hz)

Example 2

A Compound Modified by an Allyl Group at the 5-Position of the Naphthol Moiety was Synthesized.

The following compound:

[Chem. 23]

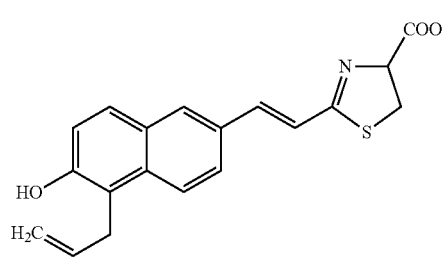

was synthesized in accordance with the following synthesis scheme.

[Chem. 24]

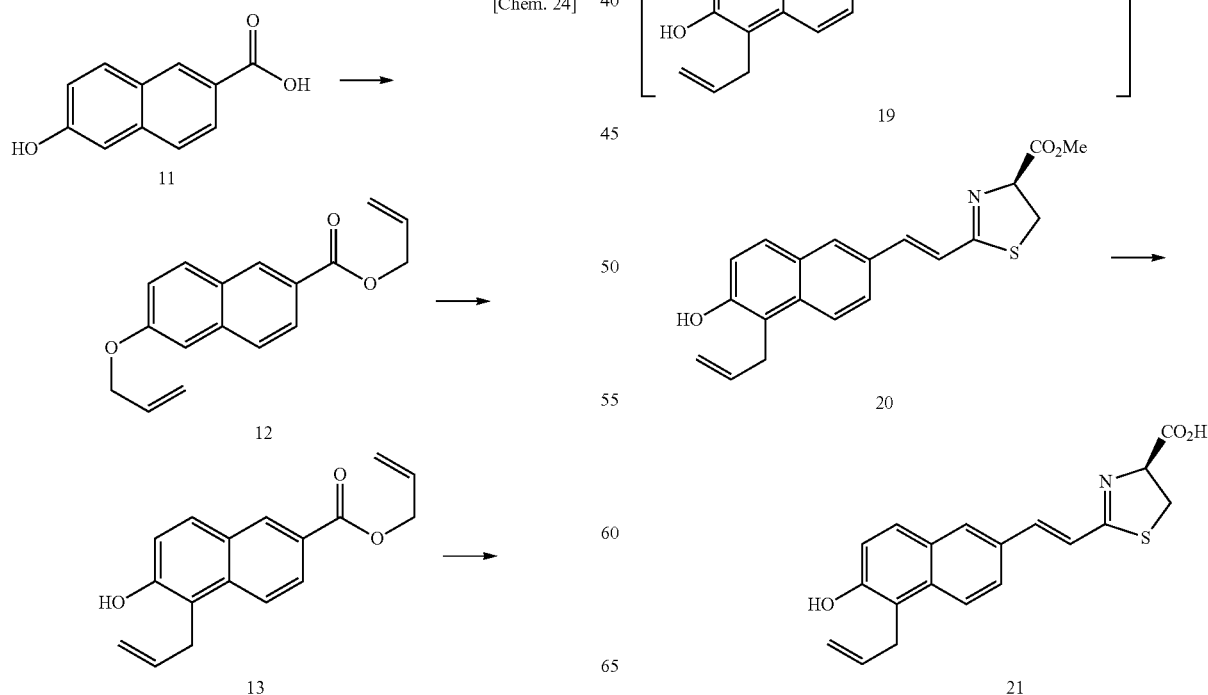

[Chem. 25]

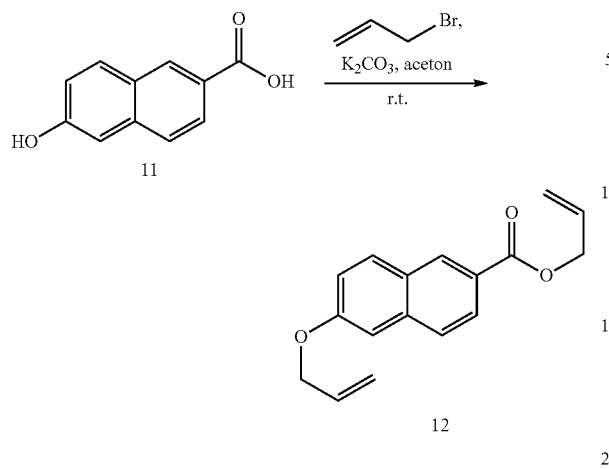

[Chem. 27]

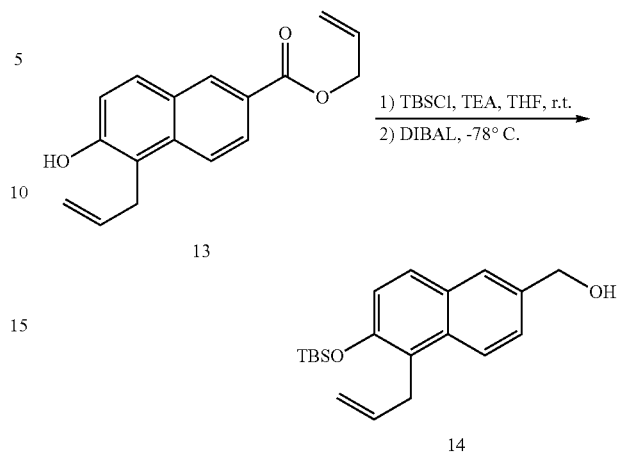

2-naphthoic acid 11 (500 mg, 2.66 mmol) was dissolved in acetone (10 ml), potassium carbonate (793 mg, 5.32 mmol) and allyl bromide (0.7 ml, 8.0 mmol) were added under ice cooling, and the reaction solution was stirred at room temperature for 1 hour. Water (100 ml) was added to the reaction solution, and after extraction with ethyl acetate, the organic layer was dehydrated with anhydrous magnesium sulfate. The solvent was distilled under reduced pressure, and the resulting crude product was purified by silica gel column chromatography (hexane:ethyl acetate=5:1), yielding compound 12 (713 mg, 100%) as a light yellow solid.

$^1$H NMR (400 MHz, CDCl$_3$) δ 4.67 (2H, d, J=4.8 Hz), 5.33 (2H, t, J=10.8 Hz), 5.46 (2H, m), 6.11 (2H, m), 7.16 (1H, d, J=2.4 Hz), 7.22 (1H, dd, J=2.4, 8.8 Hz), 7.74 (1H, d, J=8.8 Hz), 7.85 (1H, d, J=9.2 Hz), 8.04 (1H, dd, J=1.6, 8.8 Hz), 8.55 (1H, d, J=1.6 Hz)

Compound 13 (165 mg, 0.38 mmol) was dissolved in tetrahydrofuran (1 ml). At room temperature, t-butyldimethylsilyl chloride (180 mg, 1.0 mmol) and triethylamine (0.14 ml, 0.99 mmol) were added, and the result was stirred for 1 hour. After confirming the disappearance of the basic ingredient with thin layer chromatography, diisobutylaluminium hydride (1.0 M, n-hexane solution, 1.0 ml) was added to the reaction solution at −78° C., and the reaction solution was stirred for 1 hour. After raising the temperature of the reaction solution to 0° C., water (10 ml) was added, and after extraction with ethyl acetate, the organic layer was dehydrated with anhydrous magnesium sulfate. The solvent was distilled under reduced pressure, and the resulting residue was purified by silica gel column chromatography (hexane:ethyl acetate=6:1), yielding compound 14 (130 mg, 100%) in the figure as a yellow oil.

$^1$H NMR (400 MHz, CDCl$_3$) δ 0.29 (6H, s), 1.08 (9H, s), 3.85 (2H, d, 6.0 Hz), 4.77 (2H, s), 4.97 (1H, d, J=30.0 Hz), 5.01 (1H, d, J=23.2 Hz), 6.02 (1H, m), 6.02 (1H, m), 7.12 (1H, d, J=8.8 Hz), 7.44 (1H, d, J=8.8 Hz), 7.62 (1H, d, J=8.8 Hz), 7.70 (1H, s), 7.90 (1H, J=8.8 Hz)

[Chem. 26]

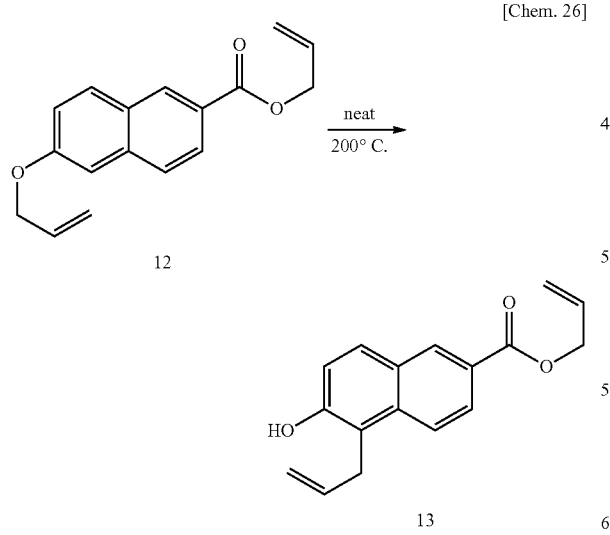

[Chem. 28]

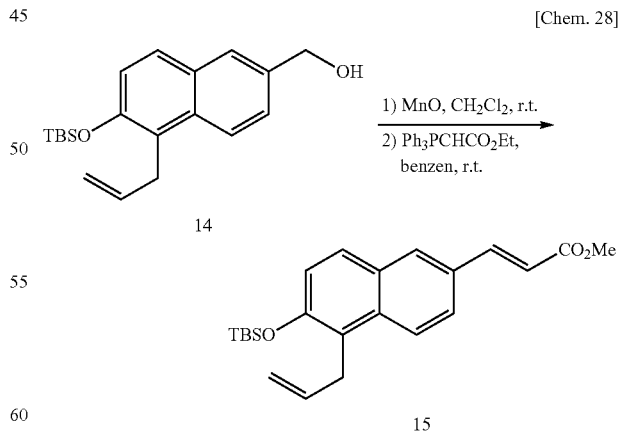

Compound 12 (760 mg, 2.83 mmol) was heated at 200° C. and stirred for 18 hours. The reaction mixture was purified by silica gel column chromatography (hexane:ethyl acetate=6:1), yielding compound 13 (546 mg, 71%) as a light yellow solid.

Compound 14 (130 mg, 0.38 mmol) was dissolved in dichloromethane (10 ml), manganese oxide (400 mg, 4.60 mmol) was added at room temperature, and the result was stirred for 4 hours. After confirming the disappearance of the basic ingredient with thin layer chromatography, impurities were removed with Celite. The solvent was distilled under reduced pressure to yield a crude product of aldehyde. The crude product was dissolved in benzene (5 ml), (carbomethoxymethylene) triphenylphosphorane (1.2 g, 3.8 mmol) was added at room temperature, and the result was stirred for 6 hours. The solvent was distilled under reduced pressure, and the resulting residue was purified by silica gel column chromatography (hexane:ethyl acetate=4:1), yielding compound 15 (145 mg, 100%) as a light yellow solid.

$^1$H NMR (400 MHz, CDCl$_3$) δ 0.26 (6H, s), 1.04 (9H, s), 3.80 (complex 5H), 4.94 (1H, d, J=38.5 Hz), 4.98 (1H, d, J=30.5 Hz), 5.99 (1H, m), 6.02 (1H, m), 6.49 (1H, d, J=16.0 Hz), 7.11 (1H, d, J=8.8 Hz), 7.64 (complex 2H), 7.84 (complex 3H)

[Chem. 29]

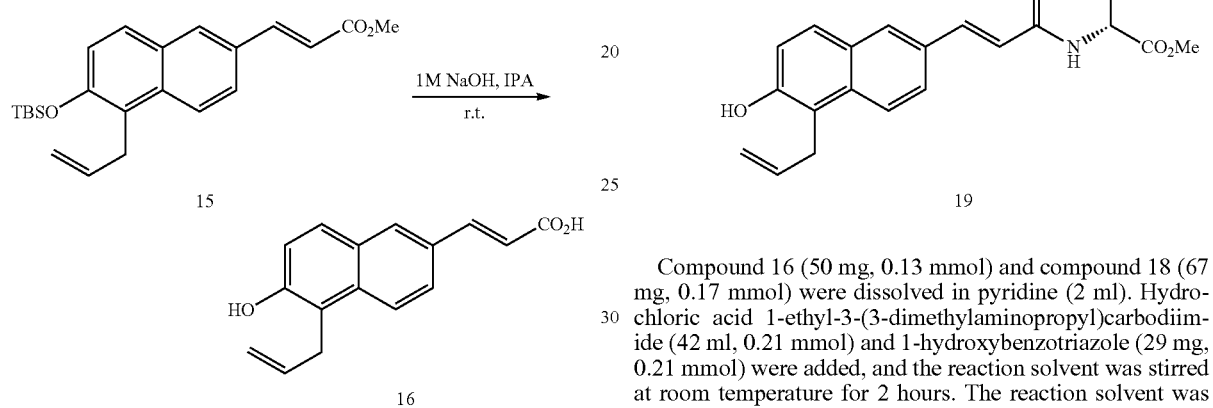

15

16

Compound 15 (53 mg, 0.14 mmol) was dissolved in isopropyl alcohol (6 ml), 1 M aqueous sodium hydroxide (3 ml, 3 mmol) was added, and the reaction solution was stirred for 12 hours at room temperature. After allowing the reaction solution to cool, cation-exchange resin (Amberlite IR-120H) was used to neutralize the reaction solution. The resin was filtered off and the solvent was distilled under reduced pressure, yielding a single product of compound 16 (51 mg, 100%) as a light yellow solid.

$^1$H NMR (400 MHz, CD$_3$OD) δ 3.83 (2H, d, J=6.1 Hz), 4.96 (complex 2H), 6.00 (1H, m), 6.56 (1H, d, J=16.0 Hz), 7.26 (1H, d, J=8.8 Hz), 7.76 (complex 3H), 8.97 (complex 2H)

[Chem. 30]

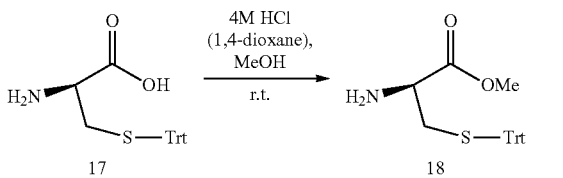

D-cysteine-5-trityl compound 17 (504 mg, 1.39 mmol) was dissolved in methanol (100 ml), and a 1,4-dioxane solution of 4 N hydrogen chloride (5.4 ml) was added. After stirring at room temperature for 17 days, cation-exchange resin Amberlite IRA400 was used for neutralization. The resin was filtered off, the solvent was distilled under reduced pressure, and the resulting residue was purified by silica gel column chromatography (hexane:ethyl acetate=1:1), yielding compound 18 (455 mg, 86%) as a light yellow oil.

$^1$H NMR (400 MHz, CDCl$_3$) δ 2.47 (1H, dd, J=8.1, 13 Hz), 2.60 (1H, dd, J=5.1, 13 Hz), 3.21 (1H, dd, J=5.1, 8.1 Hz), 3.66 (3H, s), 7.18-7.32 (9H, complex), 7.40-7.54 (6H, complex)

[Chem. 31]

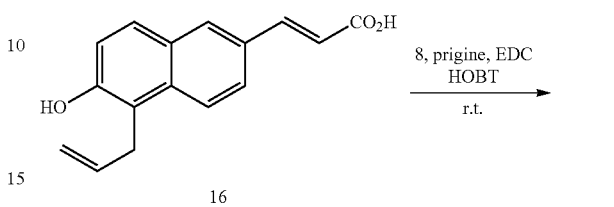

16

19

Compound 16 (50 mg, 0.13 mmol) and compound 18 (67 mg, 0.17 mmol) were dissolved in pyridine (2 ml). Hydrochloric acid 1-ethyl-3-(3-dimethylaminopropyl)carbodiimide (42 ml, 0.21 mmol) and 1-hydroxybenzotriazole (29 mg, 0.21 mmol) were added, and the reaction solvent was stirred at room temperature for 2 hours. The reaction solvent was then distilled under reduced pressure and diluted with ethyl acetate (50 ml), and water (50 ml) was added. The organic layer was cleaned with a saturated sodium chloride solution (20 ml), and the water layer was further cleaned with ethyl acetate (50 ml). The organic layer was then also dehydrated with anhydrous magnesium sulfate. The solvent was distilled under reduced pressure to yield a crude product of amide (compound 19 in the figure). Compound 19 was unstable, and the following reaction was performed without purification.

[Chem. 32]

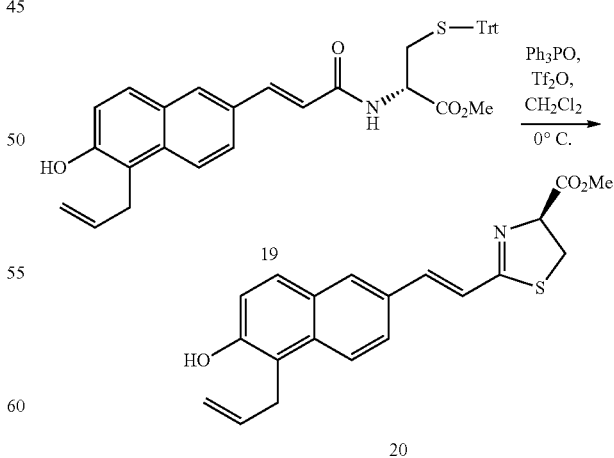

The crude product of amide (compound 19 in the figure) was dissolved in dichloromethane (35 ml), and at 0° C., triphenylphosphine oxide (106 mg, 0.37 mmol) and anhydrous trifluoromethanesulfonic acid (160 μl, 0.88 mmol) were added. After stirring for 2 hours, the reaction solution was diluted with chloroform (50 ml), and water (50 ml) was added. The organic layer was cleaned with a saturated sodium chloride solution (20 ml), and the water layer was further cleaned with ethyl acetate (50 ml). The organic layer was then also dehydrated with anhydrous magnesium sulfate. The solvent was distilled under reduced pressure, and the resulting residue was purified by silica gel column chromatography (chloroform:methanol=9:1), yielding compound 20 (36 mg, two-step yield of 80%) as a light yellow oil.

$^1$H NMR (400 MHz, CD$_3$OD) δ 3.62 (2H, m), 3.82 (complex 5H), 5.05 (complex 2H) 5.23 (1H, t, J=19.0 Hz), 6.05 (1H, m), 7.14 (complex 2H, J=8.7, 16.2 Hz), 7.26 (1H, d, J=16.2 Hz), 7.66 (complex 3H), 7.77 (1H, s), 7.86 (1H, d, J=9.0 Hz)

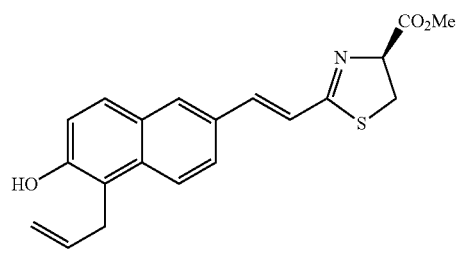

[Chem. 33]

Esterase from procine liver

20

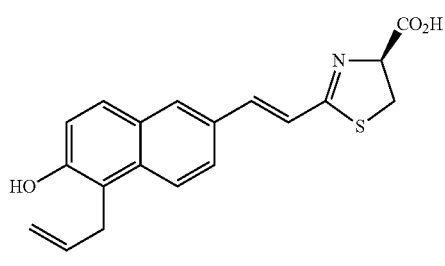

21

Compound 20 (25 mg, 0.026 mmol) was dissolved in tetrahydrofuran (1 ml), ethanol (5 ml) and a 10 mM ammonium carbonate aqueous solution (30 ml), and porcine pancreas lipase (25 mg) was added at 40° C. After stirring for 24 hours, the reaction solution was diluted with chloroform (50 ml), and water (50 ml) was added. After removing impurities with Celite, the solvent was distilled under reduced pressure. The resulting crude product was dissolved in a mixed solvent of methanol/water (1:1, 2 ml) and purified by high performance liquid chromatography (Mightsil RP-18 GP (3 μm), 0.05% TFA aq.: MeCN=9:1→1:9 (40 min), 20° C., 1 ml/min, detection 440 nm (DAD)), yielding results as in FIG. 2. Compound 21 was eluted near 19.60 min.

$^1$H NMR (500 MHz, CD$_3$OD) δ 3.62-3.70 (2H, m), 3.78 (2H, d, J=5.75 Hz), 4.90-4.95 (2H, m), 5.21 (1H, t, 8.05 Hz), 5.95-6.02 (1H, m), 7.08 (1H, m), 7.13 (1H, d, 9.15 Hz), 7.39 (1H, d, 16.0 Hz), 7.67 (1H, s), 7.67 (1H, d, 16 Hz), 7.89-7.90 (2H, m)

Reference Example 3

Synthesis of Naphthol-Monoene Type Luciferin Analog

Synthesis of TBS Protector 32

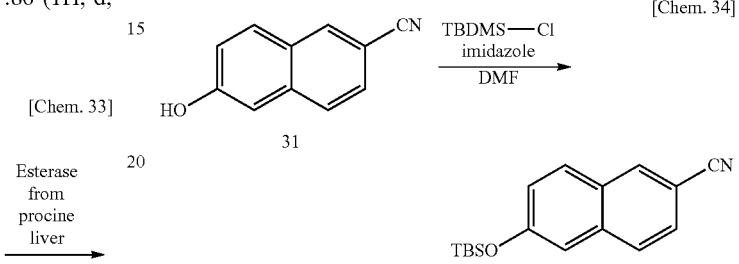

[Chem. 34]

6-cyano-2-naphthol 31 (50.2 mg, 0.297 mmol), t-butyldimethylsilyl chloride (143 mg, 0.95 mmol), and imidazole (160.7 mg, 2.37 mmol) were dissolved in DMF (0.5 mL), and the reaction mixture was stirred at room temperature for 1 hour. Water (40 mL) was added to the reaction mixture, and extraction was performed with ethyl acetate (3×60 mL). After drying the organic layer with sodium sulfate, the result was concentrated in vacuo. The resulting residue was purified by column chromatography {silica gel 36 g; hexane-ethyl acetate (8:1)}, yielding a TBS protector 32 (69.9 mg, 83%) as a colorless oil.

Analog 32
$^1$H NMR (270 MHz, CDCl$_3$) δ 0.01 (6H, s), 0.74 (9H, s), 6.80-7.80 (6H, complex)

Synthesis of Aldehyde Product 33

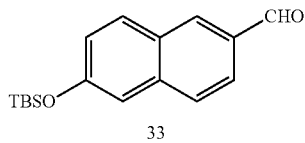

[Chem. 35]

TBS protector 32 (99.3 mg, 0.35 mmol) and 1 M diisobutylaluminium (toluene solution) 0.5 mL were dissolved in dehydrated toluene (10 mL) in an argon atmosphere, and the reaction mixture was stirred for 1 hour. The reaction mixture was cooled with ice, and then acetone (10 mL), a saturated Rochelle salt aqueous solution (20 mL), and water (30 mL) were added. Extraction was performed with ethyl acetate (3×50 mL). After adding sodium sulfate to the organic layer and drying, the result was concentrated in vacuo. The resulting residue was purified by preparative thin-layer chromatography {one 20 cm×20 cm×0.5 mm plate; hexane-ethyl acetate (10:1)}, yielding an aldehyde product 33 (74.4 mg, 74%) as a yellow oil.

Aldehyde Product 33

$^1$H NMR (270 MHz, CDCl$_3$) δ 0.28 (6H, s), 1.03 (9H, s), 7.00-7.80 (6H, complex), 10.10 (1H, s)

Synthesis of Ester Product 34

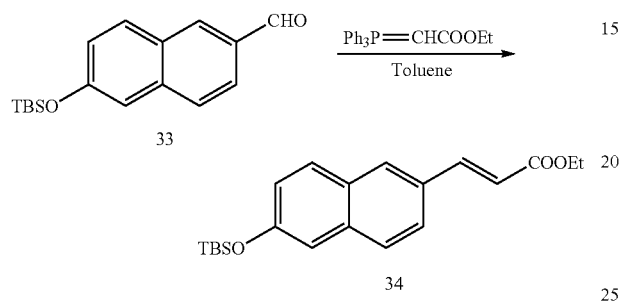

[Chem. 36]

The aldehyde product 33 (63.9 mg, 0.22 mmol) and carbethoxymethylene triphenyl phosphorane (121 mg, 0.349 mmol) were dissolved in toluene (2 mL), and the reaction mixture was stirred for 5 hours at room temperature. Water (50 mL) was added to the reaction mixture, and extraction was performed with ethyl acetate (3×50 mL). After drying the organic layer with sodium sulfate, the result was concentrated in vacuo. The resulting residue was purified by preparative thin-layer chromatography {one 20 cm×20 cm×0.5 mm plate; hexane-ethyl acetate (25:1)}, yielding an ester product 34 (76.6 mg, 97%) as a yellow oil.

Ester Product 34

$^1$H NMR (270 MHz, CDCl$_3$) δ 0.25 (6H, s), 1.00 (9H, s), 1.43 (3H, t, J=7.0 Hz), 4.23 (2H, q, J=7.1 Hz), 5.95 (1H, d, J=12.5 Hz), 6.47 (1H, d, J=16.1 Hz), 7.01-7.80 (7H, complex)

Synthesis of Carboxylic Acid 35

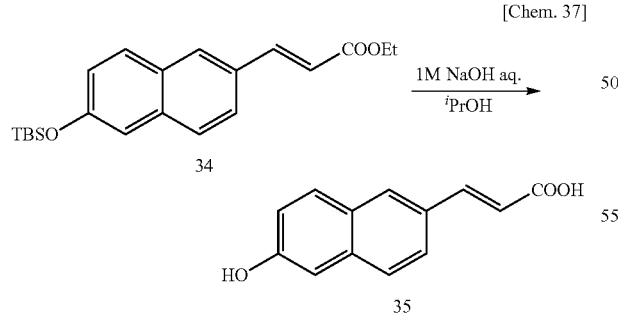

[Chem. 37]

Ester product 34 (90.8 mg, 0.253 mmol) was dissolved in isopropyl alcohol (3 mL) and 1 M aqueous sodium hydroxide (5 mL) was added. The reaction mixture was stirred for 5 hours. Cation-exchange resin Amberlite IR-120BNa was added to neutralize the reaction mixture. The resin was filtered off and the filtrate was concentrated in vacuo, yielding carboxylic acid 35 (54.9 mg, quant.) as a pale yellow solid.

Carboxylic Acid 35

$^1$H NMR (270 MHz, CD$_3$OD) δ 6.47 (1H, d, J=15.8 Hz), 7.00-7.90 (7H, complex)

Synthesis of Methyl Ester Product 36

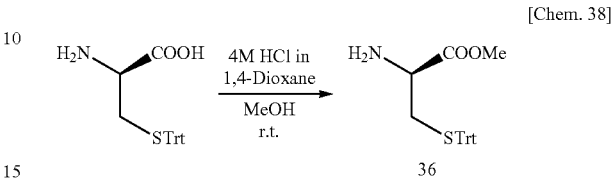

[Chem. 38]

A D-cysteine-5-trityl compound (504 mg, 1.39 mmol) was dissolved in methanol (100 ml), and a 1,4-dioxane solution of 4 N hydrogen chloride (5.4 ml) was added. After stirring at room temperature for 17 days, cation-exchange resin IRA4000H AG was used for neutralization. The resin was filtered off, and the resulting solution was concentrated in vacuo. The residue was purified by silica gel column chromatography {silica gel 33.6 g; hexane-ethyl acetate (1:1)}, yielding methyl ester product 36 (455 mg, 86%) as a pale yellow oil.

Methyl Ester 36

IR (neat) 3380, 3320, 1740, 1600 cm$^{-1}$ $^1$H NMR (270 MHz, CDCl$_3$) δ 2.47 (1H, dd, J=8.1, 13 Hz), 2.60 (1H, dd, J=5.1, 13 Hz), 3.21 (1H, dd, J=5.1, 8.1 Hz), 3.66 (3H, s), 7.18-7.32 (9H, complex), 7.40-7.54 (6H, complex)

$^{13}$C NMR (67.8 MHz, CD$_3$OD) δ 36.90 (t), 52.16 (q), 53.78 (d), 66.83 (s), 126.8 (d)×3, 127.9 (d)×6, 129.6 (d)×6, 144.5 (s)×3, 174.2 (s)

Synthesis of Amide Product 37

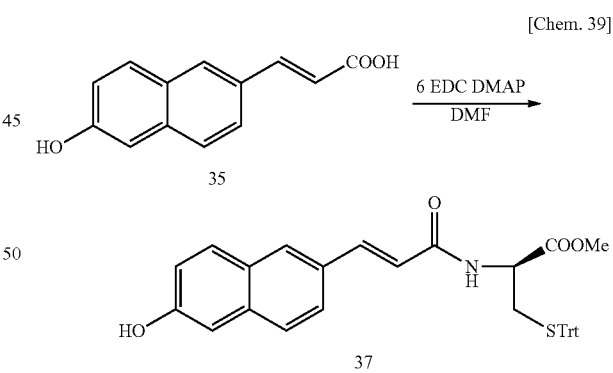

[Chem. 39]

In an argon atmosphere, carboxylic acid 35 (54.9 mg, 0.254 mmol), hydrochloric acid 1-ethyl-3-(3-dimethylaminopropyl)carbodiimide (145 mg, 0.762 mmol), and 4-dimethylaminopyridine (155 mg, 1.27 mmol) were added to an N,N-dimethylformamide solution (1 ml) of the methyl ester 36 (145 mg, 0.381 mmol), and the reaction mixture was stirred for 4 hours at room temperature. Water (50 ml) was added to the reaction mixture, and after extraction with ethyl acetate (3×50 ml) and drying of the organic layer with anhydrous sodium sulfate, the result was concentrated in vacuo. The resulting residue was purified by preparative thin-layer chromatography {two 20 cm×20 cm×0.5 mm plates; hexane-ethyl acetate (2:1)}, yielding an amide product 37 (58.4 mg, 40%) as a pale yellow oil.

Amide Product 37

$^1$H NMR (270 MHz, CDCl$_3$) δ 2.75 (2H, dd, J=4.6, 7.9 Hz), δ 3.75 (3H, s), 4.77 (1H, dd, 2.7, 7.9 Hz), 6.35 (1H, d, J=16.1 Hz), 6.90-7.80 (22H, complex)

Synthesis of Thiazoline 38

[Chem. 40]

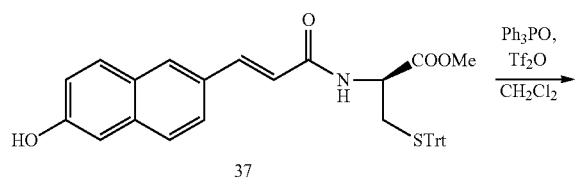

In an argon atmosphere, triphenylphosphine oxide (91 mg, 0.327 mmol) and anhydrous trifluoromethanesulfonic acid (100 μL, 0.546 mmol) were added to a dichloromethane solution (3 ml) of the amide 37 (60.3 mg, 0.109 mmol), and the reaction mixture was stirred for 1 hour at room temperature. Water (50 ml) was added to the reaction mixture, and after extraction with chloroform (3×50 ml) and drying of the organic layer with anhydrous sodium sulfate, the result was concentrated in vacuo. The resulting residue was purified by preparative thin-layer chromatography {two 20 cm×20 cm×0.5 mm plates; hexane-ethyl acetate (1:2)}, yielding a thiazoline 38 (17.4 mg, 55%) as a yellow solid.

Thiazoline 38

$^1$H NMR (270 MHz, CD$_3$OD) δ 3.63 (2H, dd, J=3.1, 8.9 Hz), 3.81 (3H, s), 5.27 (1H, t, J=8.9 Hz), 7.07-7.13 (2H, complex), 7.33 (1H, d, J=16.1 Hz), 7.55-7.83 (4H, complex)

Synthesis of Analog 39

[Chem. 41]

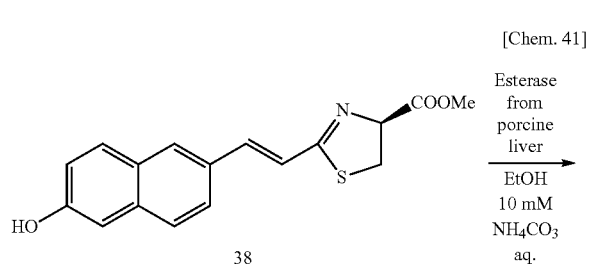

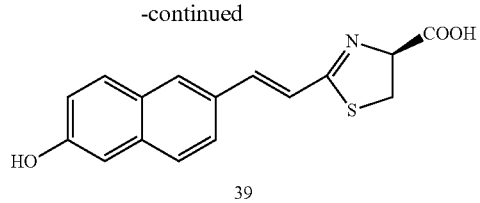

The thiazoline 38 (6.3 mg, 0.0201 mmol) was dissolved in a mixed solvent of ethanol (2 mL) and a 10 mM aqueous solution of ammonium hydrogen carbonate (8 mL), and in an argon atmosphere, a small amount of porcine liver esterase was added. After stirring at 36° C. for 17 hours, the reaction mixture was filtered, and the filtrate was concentrated in vacuo, yielding an analog 39 (7.6 mg, quant.) as a yellow solid.

Bioluminescent Emission Spectrum

In a 200 μL polystyrene tube, potassium phosphate buffer solution (0.5 M, pH 8.0, 20 μl), substrate solution (2.5 mM, 20 μl), enzyme solution (20 μl), to and ATP-Mg solution (10 mM, 40 μl) were mixed, and emission spectrum measurement was performed. An enzyme solution with a concentration of 17 μM was used. Enzymes with a concentration of 1.7 μM for the firefly luciferin and of 170 μM for the phenol-type luciferin, however, were used. The exposure time for emission spectrum measurement was 60 seconds. For the firefly luciferin, however, the time was five seconds.

Experiment Results

Using the above procedure, the emission wavelength was measured for firefly luciferin and a naphthol-monoene type luciferin analog (the above compound 39), as well as the compounds modified with an allyl group as illustrated in FIG. 1 and FIG. 2. Firefly luciferin had an emission wavelength of 565 nm. The naphthol-monoene type luciferin analog (the above compound 39) had an emission wavelength of 660 nm. The compounds illustrated in FIGS. 1 and 2 respectively had emission wavelengths of 605 nm and 690 nm. By modifying the benzothiazole ring moiety of the firefly luciferin at the 7-position with an allyl group, the emission wavelength was shifted to a longer wavelength by approximately 30 nm to 40 nm. Furthermore, by modifying the naphthol moiety of the naphthol-monoene type luciferin analog at the 5-position with an allyl group, the emission wavelength was shifted to a longer wavelength by approximately 30 nm to 40 nm.

Accordingly, it is clear that by modifying luciferin and a luciferin analog with an allyl group, the emission wavelength thereof can be shifted to a longer wavelength.

In this way, it was possible to establish an index for modifying the practical emission wavelength. By designing a luciferin derivative based on this index, a luciferase substrate with a longer emission wavelength can be manufactured.

In Vivo Bioimaging

By administering the luciferin analog according to the present invention to transgenic cells, tissue, and organisms into which luciferase has been introduced, light emission can be produced. Taking advantage of this reaction, the compound according to the present invention, which has an emission wavelength near the window into the body of 690 nm, it becomes easier to detect in vivo light emission. For example, after introducing luciferase into transplanted tissue or transplanted cells, administration of the compound according to the present invention to the animal with the transplant allows for in vivo non-invasive imaging of the status of transplanted tissue within deep portions of the organism that received the transplant, which is considered particularly difficult at present.

For in vivo imaging of cells and the like into which luciferase has been introduced, luciferase transgenic cells can be produced in accordance with the procedure described, for example, in Experimental Medicine, Vol. 26, No. 17 (special issue), 2008, pp. 110-117.

After production of luciferase transgenic cells, tissue, and organisms, the luciferin analog according to the present invention is administered for imaging of transplanted tissue or the like. Light emission by the compound according to the present invention can then be detected by a device such as an IVIS Imaging System (Xenogen Corporation).

The invention claimed is:

1. A compound of the following formula or a salt thereof:

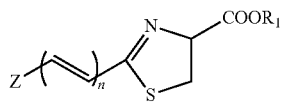

wherein
Z is

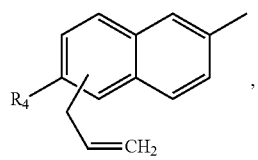

$R_1$ is H or $C_{1-4}$ alkyl,
$R_4$ is OH or $NH_2$, and
n is 0, 1, 2, or 3.

2. The compound or a salt thereof according to claim 1, wherein $R_1$ is H, and $R_4$ is OH.

3. The compound or a salt thereof according to claim 1, wherein Z is

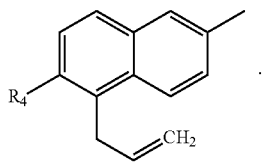

4. The compound or a salt thereof according to claim 2, wherein Z is

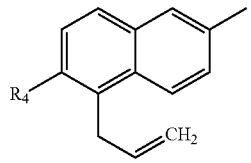

5. A luminescent substrate of luciferase, comprising the compound according to claim 1.

6. A kit for detecting luminescence, comprising the compound according to claim 1.

7. A compound of the following formula or a salt thereof:

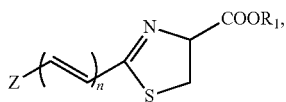

where:
Z is

$R_1$ is H or $C_{1-4}$ alkyl,
$R_4$ is OH, and
n is 0.

8. The compound or salt thereof according to claim 7, wherein $R_1$ is H.

9. A luminescent substrate of luciferase comprising the compound according to claim 7.

10. A kit for detecting luminescence comprising the compound according to claim 7.

* * * * *